United States Patent [19]

Obagi et al.

[11] Patent Number: 5,601,584
[45] Date of Patent: Feb. 11, 1997

[54] SCALPEL WITH INTEGRATED VISUAL CONTROL APERTURE

[75] Inventors: Zein E. Obagi, 9033 Wilshire Blvd., Ste. 100, Beverly Hills, Calif. 90211-1800; Anton Magnet, Seal Beach, Calif.

[73] Assignee: Zein E. Obagi, Beverly Hills, Calif.

[21] Appl. No.: 441,278

[22] Filed: May 15, 1995

Related U.S. Application Data

[63] Continuation-in-part of Ser. No. 139,777, Oct. 22, 1993, abandoned.

[51] Int. Cl.$^6$ ........................................... A61B 17/32
[52] U.S. Cl. ................................. 606/172; 128/751
[58] Field of Search .................. 606/167, 172; 128/751

[56] References Cited

U.S. PATENT DOCUMENTS

| | | |
|---|---|---|
| 1,239,419 | 9/1917 | Marx . |
| 1,516,071 | 11/1924 | Apolant . |
| 1,935,605 | 11/1933 | Altruda . |
| 2,236,067 | 3/1941 | Poth . |
| 2,419,114 | 4/1947 | Briegel . |
| 2,426,381 | 8/1947 | Vermillion . |
| 2,457,772 | 12/1948 | Brown et al. . |
| 2,540,462 | 2/1951 | Smith . |
| 2,582,511 | 1/1952 | Stryker . |
| 3,415,251 | 12/1968 | Knapp et al. . |
| 3,428,045 | 2/1969 | Kratzsch et al. . |
| 3,670,733 | 6/1972 | Carlisle . |
| 3,670,734 | 6/1972 | Hardy, Jr. . |
| 3,797,505 | 3/1974 | Gilhaus et al. ................ 132/76.4 |
| 3,934,591 | 1/1976 | Gleason . |
| 3,945,117 | 3/1976 | Beaver ........................... 30/287 |
| 4,038,986 | 8/1977 | Mahler . |
| 4,098,278 | 7/1978 | Schwartz . |
| 4,221,222 | 9/1980 | Detsch . |
| 4,270,540 | 6/1981 | Schwartz . |
| 4,542,742 | 9/1985 | Winkelman et al. . |
| 4,569,133 | 2/1986 | Schmidt ........................... 30/293 |
| 4,682,597 | 7/1987 | Myers .............................. 606/172 |
| 4,690,139 | 9/1987 | Rosenberg . |
| 4,759,363 | 7/1988 | Jensen . |
| 5,026,385 | 6/1991 | Schutte et al. .................. 606/167 |
| 5,071,427 | 12/1991 | Stahl ................................ 606/172 |
| 5,250,064 | 10/1993 | Schneider ..................... 606/172 X |

FOREIGN PATENT DOCUMENTS 1232249  5/1986  U.S.S.R. .

Primary Examiner—Michael Powell Buiz
Assistant Examiner—Nancy Connolly Mulcare
Attorney, Agent, or Firm—Brown, Martin, Haller & McClain

[57] ABSTRACT

A scalpel is disclosed for the accurate and rapid formation of flaps or thin sections of skin during many types of surgical procedures (such as excision or reconstruction) in which it is necessary for the surgeon to make an oblique extended cut into the patient's skin and lift an elongated flap of the outer layers of the skin to obtain access to deeper layers of tissue, muscle or bone below. The scalpel has an elongated handle having two opposite ends; a cutting blade extending laterally from one of the ends; and a depth-of-cut limiting plate extending laterally from the same end and disposed parallel to and spaced apart from the cutting blade. The limiting plate has an aperture therein through which the surgeon can view the cutting blade during use. The scalpel thus limits the maximum thickness of tissue that can be cut with the cutting blade. The blade and limiting plate are mounted substantially at a right angle to the axis of the scalpel are angled upwardly or downwardly, preferably upwardly, and can be adhered to the surface of the handle in any suitable manner. The blade and apertured plate are normally spaced apart by a dimension on the order of about 0.02"–0.06" (0.5–1.5 mm). It is contemplated that there may be sets of scalpels with a range of spacing intervals scaled in suitable increments.

11 Claims, 1 Drawing Sheet

SCALPEL WITH INTEGRATED VISUAL CONTROL APERTURE

CROSS-REFERENCE TO RELATED APPLICATION

This application is a continuation-in-part of application Ser. No. 08/139,777, filed Oct. 22, 1993, of like title, now abandoned.

BACKGROUND OF THE INVENTION

1. Field of the Invention

The invention herein relates to scalpels. More particularly it relates to scalpels useful for thin section surgery.

2. Description of the Prior Art

There are numerous surgical procedures (such as excision or reconstruction) in which it is necessary for the surgeon to make an oblique extended cut into the patient's skin and lift an elongated flap of the outer layers of the skin to obtain access to deeper layers of tissue, muscle or bone below. Once the desired surgical procedure is completed on the underlying tissue, muscle or bone, the flap (or "thin section") of the outer layers of the skin can then be replaced in its original position. The patient's skin then heals with little or no scarring or other indication of the surgery, since the only external trauma to the skin has been the single oblique scalpel cut, which is thin and is expected to heal readily and essentially invisibly.

In the past, however, it has not been possible with existing scalpels for surgeons to make such oblique cuts uniformly, cleanly and evenly. Conventional scalpels have been designed for perpendicular (vertical) cuts into the skin. If a surgeon wants to make an oblique cut, obtaining the desired angle and depth of the cut with a conventional scalpel requires exceptional manipulative skill by the surgeon to control the scalpel. In most cases, particularly with longer cuts and because of the flexibility and elasticity of skin, the result is a flap or thin section of non-uniform thickness, and a detrimental effect to the patient. The uneven angle of the cut can result in trauma to skin layers other than those intended to be cut. Similarly, the uneven thicknesses of the flap itself can lead to differential healing of the various segments of different upper skin layers. Both of these in turn can cause the resultant effect that upon healing an undesirable amount of visual indication of the prior surgery, such as scarring, still remains. This is particularly critical where cosmetic or reconstructive facial surgery is involved, since the goal of such surgery is to restore a natural unscarred appearance to the patient.

SUMMARY OF THE INVENTION

The unique scalpel of this invention therefore provides great advantage to surgeons, since unlike any prior surgical scalpels, blades or other handheld devices, it permits accurate and rapid formation of flaps or thin sections of skin during many types of surgical procedures. This enables surgeons to make a clean, uniform oblique cut and release a uniform think flap of the skin, so that the muscle and other tissue structures under the surface flap can be exposed and accessed. Once the surgery on the underlying structures has been completed, the flap can then be replaced, and because of its uniform thickness and the clean cut of its edges, it will heal with a minimum of visual indication of the surgery.

In its broadest aspect, the invention is a scalpel as for thin section surgery to a patient's skin comprising an elongated handle having two opposite ends, a top, a bottom, and opposed sides connecting the top and bottom, the disposition of such all being defined with reference to the orientation of the scalpel when in the grip of a user; a cutting blade extending laterally from the handle beyond one of the sides at one of the ends; and depth-of-cut limiting means extending laterally from the handle beyond the one of the sides from the one of the ends and disposed parallel to and spaced apart from the cutting blade, the limiting means also having an aperture therein; whereby in use during the thin section skin surgery the cutting blade is oriented generally parallel to a surface of the skin, the limiting means limits the maximum thickness of skin tissue that can be cut with the cutting blade; and progress of the cut of the scalpel during the surgery can be visually monitored by the user through the aperture.

The blade and limiting means (a plate) are mounted substantially at a right angle to the axis of the scalpel, are angled upwardly or downwardly (preferably upwardly) and can be adhered to the surface of the handle in any suitable manner, as for instance by an adhesive, by welding or by a mechanical fastener. The cutting portion of the blade is angled upwardly or downwardly by about 15°–45°, preferably 15°–25°. The cutting portion of the blade and the viewing portion of the limiting plate are normally spaced apart by a dimension on the order of about 0.02"–0.06" (0.5–1.5 mm).

DETAILED DESCRIPTION AND PREFERRED EMBODIMENTS

Figure 1:
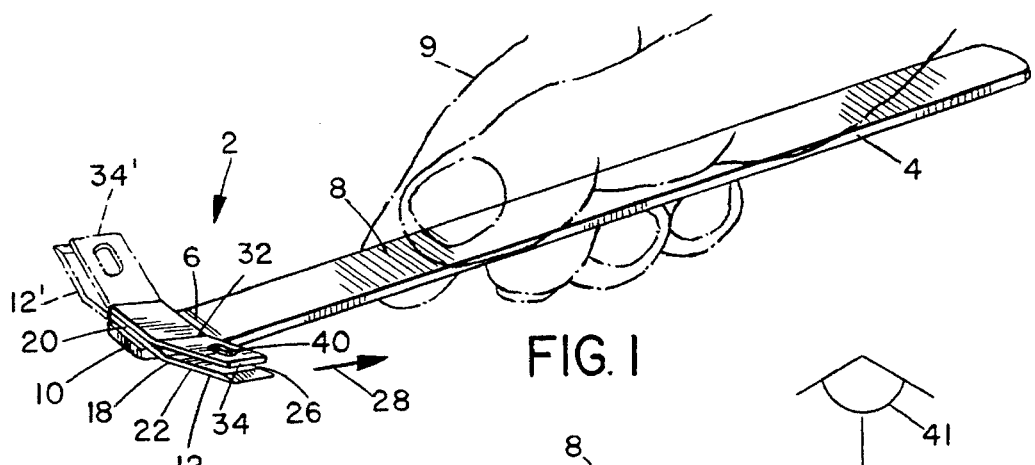
FIG. 1 is a perspective view of one preferred embodiment of the scalpel of this invention, also illustrating its manner of use.
Figure 4:
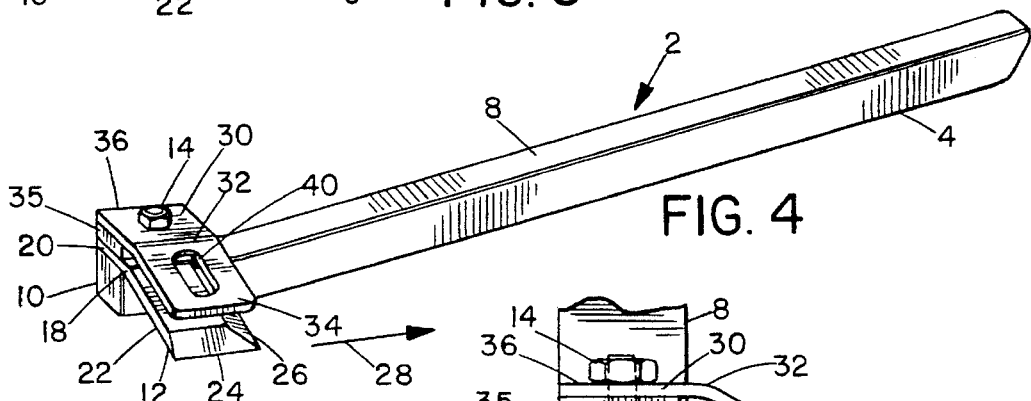
FIG. 4 is a perspective view of an alternative embodiment of the scalpel of this invention.
Figure 5:
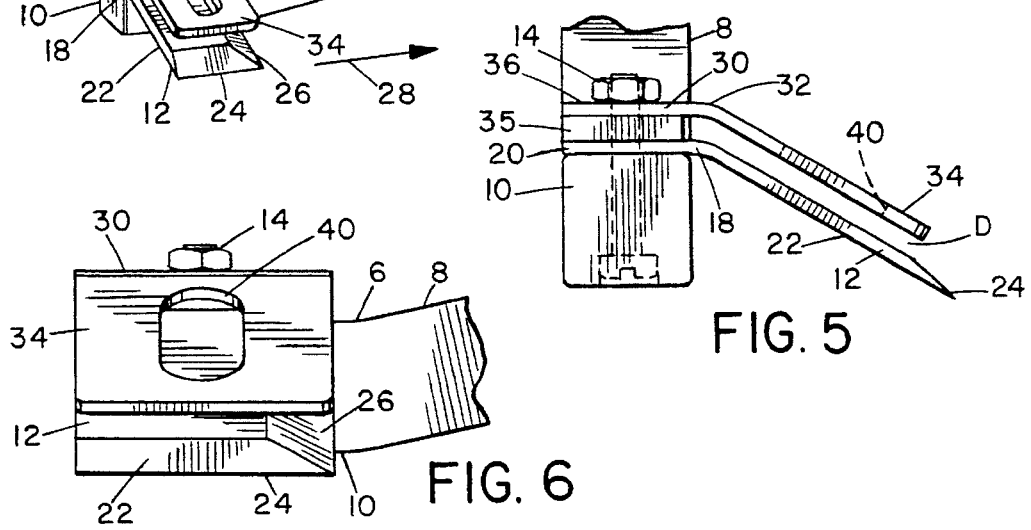
FIG. 5 is an enlarged end elevation view of the scalpel of FIG. 4.

The scalpel of the present invention is best understood by reference to the drawings. The scalpel 2 has an elongated handle 4 which is of a length and shape designed to fit comfortably in a surgeon's hand 9. Typically the handle will be on order of 4"–6" (10–15 cm) in length. The width and depth may be of any desired dimensions which will provide sufficient stiffness and strength to the handle while being easily gripped by the surgeon; typically each of these will be in the range of about 0.125"–0.50" (3–12 mm). Typical shapes for the handle with width and depth illustrated generally in proportion to length are shown in FIGS. 1 and 4.

Near one end of the handle 4 is an angular offset 6 which divides the handle 4 into a long gripping section 8 and a short blade mounting section 10. The blade mounting section 10 is normally equal to or just slightly greater in length than the width of the scalpel blade 12. The angle of the offset is usually in the range of about 15°–25°, but other angles can be used at the preference of the surgeon.

Figure 2:
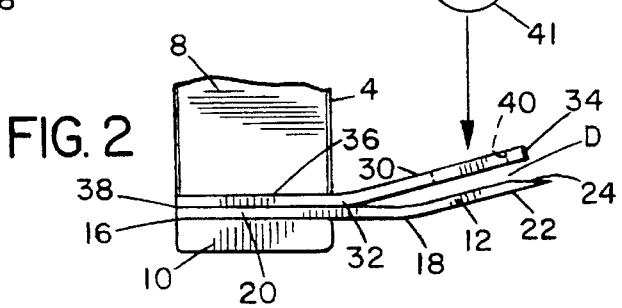
FIG. 2 is an enlarged end elevation view of the scalpel of FIG. 1, also illustrating visual observation of a cut when the scalpel is in use.

The scalpel blade 12 is mounted substantially at a right angle to the axis of the handle 4 and is adhered to the surface of the blade mounting portion 10 in any suitable manner, as for instance by an adhesive, by welding or by a mechanical fastener such as bolt-and-nut 14. Having an adhesive bond or welded bond at interface 16 between blade 12 and blade mounting portion 10, as illustrated in FIG. 2, is preferred for simplicity of construction and ease of sterilization between uses. However, the embodiment shown in FIG. 4 with a mechanical fastener such as bolt-and-nut 14 may be preferred where it is desired to have the ability to interchange blades; a similar structure (not shown) would be a bolt threaded into a corresponding threaded socket in blade mounting portion 10 or a slot into which replaceable blades 12 could be fitted.

The orientation of the blade with respect to the surgeon and surgeon's hand 9 is critical. When the surgeon holds the scalpel 2 in the normal grip, the blade 12 must extend outward from the side of the handle, so that the blade 12 will be substantially parallel to the skin of the patient. Thus, as illustrated in FIG. 1, the blade 12 will extend sideways from the handle so that it can be viewed by the surgeon as the cut is made, as will be described below. Other orientations, such as having the blade extend downwardly from the handle (from the perspective of the surgeon) defeats the purpose of the invention, since the blade 12 in such orientation is not visible to the surgeon, as will be evident from FIG. 2. Therefore, in FIG. 1 the blade 12 (and the plate 30 described below) is shown as extending laterally to the left of the handle axis with the blade 12 on top of the handle. Since the blade 12, as described below, is intended to cut as the scalpel 2 is pulled in the direction of arrow 28 by the surgeon, the left-extending blade 12 is what would be used when the surgeon holds the scalpel 2 in the right hand 9. The blade 12 may be alternatively mounted extending to the right, as shown in phantom at 12' (with plate 30'), when the scalpel 2 is to be held in the left hand. Also, although not preferred, the blade 12 and plate 30 can be attached to the underside of mounting portion 10.

Figure 3:
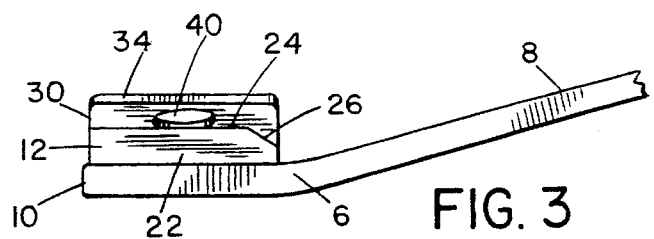
FIG. 3 is an enlarged side elevation view of the blade and guide structure of the scalpel of FIG. 1.
Figure 6:
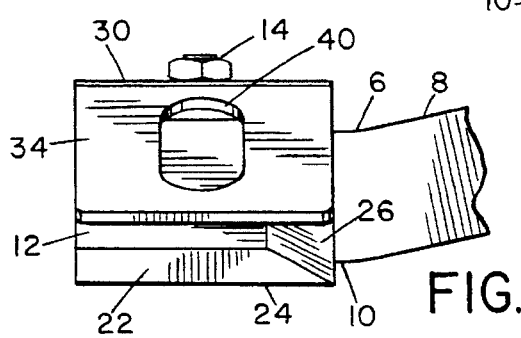
FIG. 6 is an enlarged side elevation view of the alternative blade and guide structure of the scalpel of FIG. 4.

Blade 12 has an angular offset 18 which divides the blade into a mounting portion 20 and cutting portion 22, mounting portion 20 being the portion of the blade 12 which is in contact with handle 4's mounting portion 10. The mounting portion 20 of blade 12 has a length essentially equal to the width of handle 4, while the cutting portion 22 has a length usually in the range of about 0.25"–0.50"(6–12 mm); the width of the blade 22 is usually in the range of about 0.20"–0.35" (5–9 mm). Because of the angular offset 18, the cutting portion 22 of blade 12 is directed upwardly or downwardly, with respect to the orientation of the blade mounting portion 10, as illustrated in FIGS. 3 and 6. The degree of the upward or downward angle will be predetermined, and commonly will be and preferably 15°–25°. The angle selected and the length of the cutting portion 22 of blade 12 determine the angle and depth of the cut to be made in the patient's skin. It is preferred that the blade angle upwardly as shown in FIGS. 1–3, since that results in the most comfortable position for the surgeon to hold the scalpel. Cutting portion 22 is beveled on its distal end 24 and inward edge 26 to form cutting edges equivalent to the cutting edges of conventional scalpel blades. As noted, the scalpel thus cuts as it is drawn by the surgeon in the direction indicated by arrow 28.

Positioned directly above and disposed essentially parallel to blade 12 is a depth-of-cut limiting plate 30. Plate 30 also has an angular offset 32 which divides the plate 30 into viewing portion 34 and mounting portion 36. Mounting portion 36 functions in the same manner as mounting portion 20 of blade 12 and is similarly secured to blade 12 by adhesive or welding at interface 38 or by bolt-and-nut 14. The mounting portions 20 and 36 may be in abutting relationship as indicated in FIG. 2 or may be separated by a spacer 35. The position and angle of angular offset 32 are designed such that viewing portion 30 becomes disposed parallel to cutting portion 22 of blade 12 and is spaced apart therefrom by a dimension D. Dimension D represents the maximum thicknesses of the flap or thin section of skin which the scalpel 12 of the present invention is to cut. Thus, viewing portion 34 serves as a maximum depth-of-cut limiting device and simultaneously serves to keep that depth of cut at a constant amount so that the flap will have substantially uniform thickness equivalent to dimension D. Dimension D is commonly on the order of about 0.02"–0.06" (0.5–1.5 mm). It is contemplated that there may be sets of scalpels with a range of dimensions D between the blade's cutting portion 22 and the plate's viewing portion 34, with the intervals between the dimensions D being scaled in suitable increments, such as tenths of millimeters or hundredths of inches.

Also present in the limiting portion 34 of the blade 30 is viewing aperture 40. The presence of aperture 40 allows the surgeon to maintain close visual control of the cut (as indicated at 41) and to insure that the cut proceeds smoothly without snagging or compressing the skin, so that the ultimate surgical cut line visible on the surface of the patient's skin is even and smooth. Aperture 40 is shown in the figures as oval shaped, but it could of course be any of a number of other shapes including circular, rectangular, elliptical or the like. The dimensions of the aperture 40 should be such that there is ample area of the surgeon to view the progress of the incision but not so great that the strength and positioning of the limiting plate 30 is adversely affected; typically the aperture will have a viewing area on the order of about 0.03 in$^2$ (0.20 cm$^2$).

Aperture 40 also permits the surgeon to control depth of cut less than the maximum equal to dimension D if so desired, since the skin can be constantly viewed as the cut progresses. Excessive depth-of-cut will be avoided, since the presence of plate 30 limits the thickness of the flap to the dimension D.

The angle of offset 6 is on the order of about 15° to 30°. It may be varied, however, to determine the most comfortable angle for the surgeon to hold the scalpel by blade 4 while forming a smooth even cut in the direction of the arrow 28 with the end portion 10 being maintained substantial level and parallel to the skin surface.

The scalpel 2 and blade 12 may be made from any material conventionally used for scalpels and blades of all types. Stainless steel or surgical steel are examples of such typical materials.

It will be evident from the above description that there are numerous embodiments of the invention which, while not expressly described above, are clearly within the scope and spirit of the invention. The above description should therefore be considered to be exemplary only, and the scope of the invention is to be determined solely by the appended claims.

We claim:

1. A scalpel as for thin section surgery to a patient's skin comprising:

an elongated handle having two opposite ends, a top, a bottom, and opposed sides connecting said top and bottom, the disposition of such all being defined with reference to the orientation of said scalpel when in the grip of a user;

a cutting blade extending laterally from said handle beyond one of said sides at one of said ends; and depth-of-cut limiting means extending laterally from said handle beyond said one of said sides from said one of said ends and disposed parallel to and spaced apart from said cutting blade, said limiting means also having an aperture therein;

whereby in use during said thin section skin surgery said cutting blade is oriented generally parallel to a surface of said skin, said limiting means limits the maximum thickness of skin tissue that can be cut with said cutting blade; and progress of the cut of said scalpel during said surgery can be visually monitored by said user through said aperture.

2. A scalpel as in claim 1 wherein said elongated handle has an angular offset near said end at which said cutting blade is located, said offset dividing said handle into two portions, the portion of said handle from which said cutting blade extends being angled to the remaining portion of said handle.

3. A scalpel as in claim 2 wherein the angle of offset is in the range of about 15°–25°.

4. A scalpel as in claim 1 wherein said laterally extending cutting blade has an angular offset which divides said blade into a connecting portion connected to said handle and a cutting portion spaced apart from said handle, whereby by means of said offset said cutting blade makes a bias cut in use.

5. A scalpel as in claim 4 wherein said angular offset in said cutting blade has an angle in the range of 15°–45° with reference to the orientation of said cutting portion of said cutting blade to said handle.

6. A scalpel as in claim 5 wherein said angular offset in said cutting blade has an angle of about 15°–25°.

7. A scalpel as in claim 4 wherein said cutting portion of said cutting blade is angled upwardly with respect to said end portion of said handle when said scalpel is in use.

8. A scalpel as in claim 4 wherein said cutting portion of said cutting blade is angled downwardly with respect to said end portion of said handle when said scalpel is in use.

9. A scalpel as in claim 4 wherein said limiting means has an angular offset corresponding to said angular offset of said cutting blade and which divides said limiting means into a connecting portion connected to said handle and a viewing portion spaced apart from said handle.

10. A scalpel as in claim 9 wherein said aperture is in said viewing portion of said limiting means.

11. A scalpel as in claim 10 wherein viewing portion has a thin blade-like configuration with top and bottom bounded surfaces and said aperture is generally centered within said bounded viewing portion.

* * * * *